United States Patent [19]

Ragg

[11] Patent Number: 4,849,349
[45] Date of Patent: Jul. 18, 1989

[54] GENES FOR BIOLOGICALLY ACTIVE PROTEINS

[75] Inventor: Hermann Ragg, Kelkheim, Fed. Rep. of Germany

[73] Assignee: Hoechst Aktiengesellschaft, Frankfurt am Main, Fed. Rep. of Germany

[21] Appl. No.: 826,734

[22] Filed: Feb. 6, 1986

[30] Foreign Application Priority Data

Feb. 8, 1985 [DE] Fed. Rep. of Germany ....... 3504334
Jun. 13, 1985 [DE] Fed. Rep. of Germany ....... 3521226

[51] Int. Cl.⁴ ...................... C12N 15/00; C12N 1/00; C12P 21/00
[52] U.S. Cl. .................................. 435/68; 435/172.3; 435/320; 435/91; 435/317.1; 935/6; 935/8; 935/9; 935/10; 935/11; 935/29
[58] Field of Search ............ 435/68, 91, 172.3, 317.1, 435/320; 935/6, 8, 9, 10, 11, 29

[56] References Cited

FOREIGN PATENT DOCUMENTS 0090505 5/1983 European Pat. Off. .
0120829 3/1984 European Pat. Off. .

OTHER PUBLICATIONS

Chandra et al., Proc. Natl. Acad. Sci., vol. 80, 1845–1848, Apr. 1983.
Rosenberg et al., Nature, vol. 312 1, pp. 76–88, Nov. 1984.
Kurachi et al., Proc. Natl. Acad. Sci., vol. 78 11, pp. 6826–6830, Nov. 1981.
Stackhose, R. et al., "Purification of Antithrombin III mRNA and Cloning of Its cDNA", J. Biol. Chem. 258:703–706, 1982.
Witt, I. et al., "Amino Acid Composition and N-Terminal Sequence of Antithrombin BM", Thrombosis Research 32:513–518, 1983.
Courtney, M. et al., "Synthesis in *E. coli* of 1-Antitrypsin Variants of Therapeutic Potential for Emphysema and Thrombosis", Nature 313: 149–151.

Primary Examiner—Thomas G. Wiseman
Assistant Examiner—Patricia Carson
Attorney, Agent, or Firm—Finnegan, Henderson, Farabow, Garrett and Dunner

[57] ABSTRACT

The cDNA of a new proteinase inhibitor was isolated from a cDNA library of human liver biopsy material using a synthetic Oligonucleotide probe. The cDNA can be expressed by introduction of the cDNA to a microbial host on a DNA vector. Analogs of known proteinase inhibitors can be producing by alteration of the cDNA by substituting codons in the active center of the new proteinase inhibitor.

18 Claims, 1 Drawing Sheet

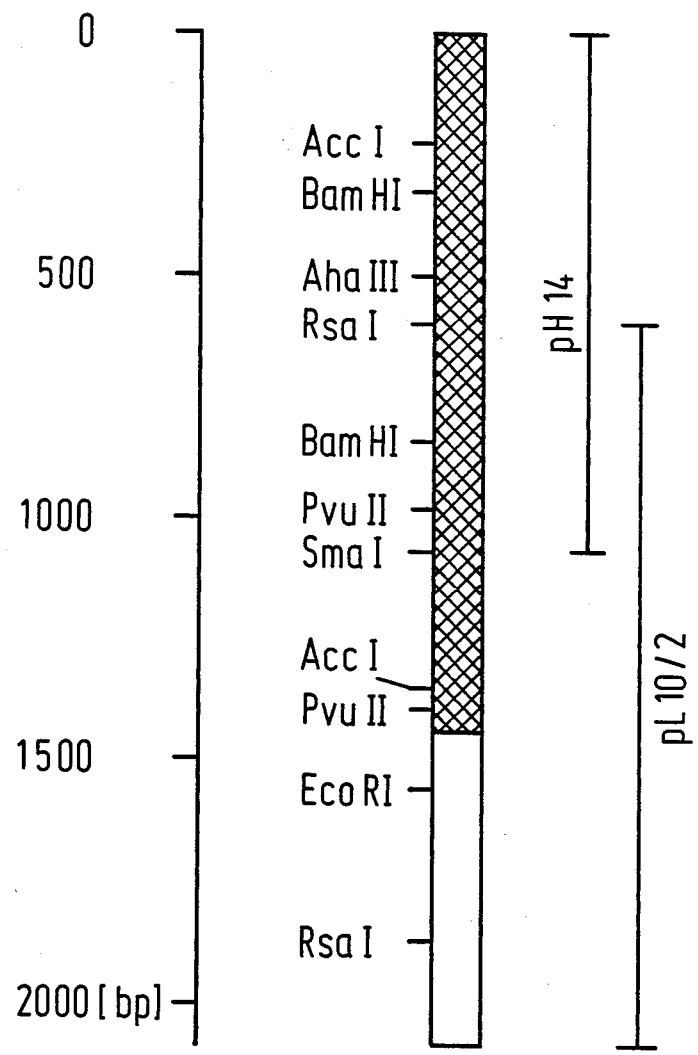

GENES FOR BIOLOGICALLY ACTIVE PROTEINS

The invention relates to a new member of the gene family which has hitherto comprised the genes for the proteinase inhibitors antithrombin III, $\alpha_1$-proteinase inhibitor ($\alpha_1$-antitrypsin), antichymotrypsin, contrapsin and $\alpha_2$-antiplasmin, and by angiotensinogen.

BRIEF DESCRIPTION OF THE DRAWINGS

FIG. 1 is an amino acids sequence of the present invention.

FIG. 2 is a nucleotide sequence of the present invention.

DESCRIPTION OF THE PREFERRED EMBODIMENTS

The gene which has been found codes for a protein with the amino acid sequence I (annex). Its coding strand has 2081 nucleotides, 636 of these being located after the stop codon TAG (DNA sequence I). In the figure, the nontranslated region is represented as an unshaded block, and the structural gene is represented by shading. The DNA sequence I contains an additional two nucleotides upstream of the codon for the N-terminal amino acid (glycine), which presumably code for the final amino acid of a prosequence (by analogy with the proteinase inhibitors AT BM and heparin cofactor II, it is possible to conclude that glycine is the N-terminal amino acid of the "mature" new proteinase inhibitor: I. Witt et al., Thrombosis Research 32 (1983) 513–518; M. J. Griffith et al., J. Biol. Chem. 260 (1985) 2218–2225).

Amino acid sequence I allows those skilled in the art to prepare antibodies in a known manner, by selection of oligopeptides from this amino acid sequence I, to load an antibody column with them, and to use this column to isolate the complete protein from biological material.

On the other hand, it is possible to use the gene or the cDNA sequence I to express the protein in suitable host organisms.

It is furthermore possible to derive from the amino acid sequence I modified genes or partial genes which lead to modified proteins in which individual amino acids have been exchanged, deleted or introduced. It is also possible in the construction of synthetic genes to provide new recognition sites for restriction enzymes, which permit further modifications of the amino acid sequence. It is also possible to take into account in the construction of synthetic genes the fact that, compared with higher organisms, microbial host organisms in some cases prefer other codons.

The new protein exhibits homologies with the above-mentioned proteinase inhibitors, at the level both of the DNA and of the amino acid sequence. For this reason, the gene is also suitable for the preparation of analogs of proteinase inhibitors by replacement of the nucleotides coding for the "active center" of the new protein by the appropriate nucleotides coding for the "active centers" of the known proteinase inhibitors. The "active center" of the new protein comprises the amino acids Leu-Ser (amino acids 444 and 445 of amino acid sequence I), corresponding to the nucleotide sequence CTG TCC.

Thus, in this type of construction of analogs of known proteinase inhibitors it is possible, by the "modular principle", for a partial gene I which codes for the amino acid sequence upstream of the active center to be combined with a partial gene II which codes for the amino acid sequence downstream of the active center, with interpolation of a gene fragment which codes for the appropriate active center. In this process it is possible to make use of the following recognition sites for restriction enzymes in the DNA sequence I:

Sau3A I ( ↓ GATC, positions 1271–1274), Acc I

positions 1356–1361) or Taq I (T ↓ CGA, positions 1246–1249 and 1357–1360).

The modification of humane $\alpha_1$-antitrypsin has already been disclosed (S. Rosenberg et al., Nature 312 (1984) 77–80, compare A. Maelicke, Nachr. Chem. Tech. Lab. 32 (1984) 1070; M. Courtney et al., Nature 313 (1985) 149–151), in each case the active center having been modified but the amino acid sequences upstream and downstream of the active center remaining unchanged. In contrast, the new products obtained according to the invention have amino acid sequences upstream and downstream of the active center which correspond to the new proteinase inhibitor and, where appropriate, its modifications, but contain the active center of another proteinase inhibitor. Thus the invention permits a multiplicity of modifications of such proteins, all of which have virtually the same tertiary structure. Their biological activity is influenced by the active center.

In one embodiment of this invention, a protein with proteinase inhibitor activity is disclosed which has amino acids 1 to 443 and/or 446 to 480 of amino acid sequence I.

The new protein and its analogs have proteinase-inhibitory, in particular thrombin-inhibitory, activity and they influence the coagulation of blood. Thus they can be used as medicaments in a daily dose from about 0.1 to 100 mg. Since, as is known, proteins are broken down in the stomach, the proteins according to the invention must be administered in a medicament form which prevents this breakdown, for example by administration in the form of enteric capsules or by parenteral administration.

The cDNA sequence I was obtained by screening of a human liver cDNA bank using the oligonucleotide, obtained by synthesis, of DNA sequence II

5' GGGTTGGCTACTCTGCCCATGAAGA 3'.

This nucleotide sequence was selected with reference to the known cDNA sequence of proteinase inhibitors adjacent to the carboxyl terminal end. It has emerged that the sequence is substantially complementary to the coding strand corresponding to amino acids 469 to 477 of amino acid sequence I.

The methods for the synthesis of oligonucleotides, for the hybridization and for the obtaining of the gene are generally known, as are the procedure for the introduction of the genetic information into host cells and the expression of the coded polypeptide in prokaryotic and eukaryotic expression systems. Prokaryotic cells produce the protein in the non-glycosylated state, whereas eukaryotic systems are able to generate a glycosylated protein. N-Glycosylation can take place at amino acids 30, 169 and 368 of amino acid sequence I.

The modification of DNA sequence I is illustrated below by the example of the introduction of another active center. For this purpose, DNA sequence I is partially cut with endonucleases Sau3A I and AccI, and the short DNA fragment is replaced by a synthetically prepared gene fragment which codes for the following active centers:

| Amino acid sequence | proteinase inhibitor activity |
|---|---|
| Arg—Ser | as antithrombin III (human) |
| Met—Ser | as $\alpha_1$-antitrypsin (human) |
| Val—Ser | as $\alpha_1$-antitrypsin |
| Lys—Ala | as mouse-contrapsin |
| Try—Ser | as mouse-$\alpha_1$-antitrypsin |
| Leu—Met | as $\alpha_2$-antiplasmin |

(R. Hill et al., Nature 311 (1984) 175–177; M. Courtney et al., loc. cit.; J. Travis et al., Behring Inst. Mitt. 73 (1983) 56–65).

The DNA sequence I can also be modified by addition of a nucleotide sequence coding for a signal peptide according to known methods.

Thus the new gene is also suitable as a starting material for the preparation of new proteins with proteinase-inhibitory activity. These new compounds can also be used as medicaments corresponding to the known proteinase inhibitors which have identical or similar actions.

It is also possible to modify further these new analogs of known proteinase inhibitors by modification of the gene in a known manner, by which means there are obtained proteins in whose amino acid chain amino acids have been replaced, deleted or added to. The invention likewise relates to proteins of this type with proteinase inhibitor activity.

The specific aspects of the invention are illustrated in detail in the examples which follow. Unless otherwise stated, percentages relate to weight.

EXAMPLE 1

Isolation of the RNA

Frozen human liver biopsy material was powdered under liquid nitrogen in a mortar. The powder was homogenized in a mixer with 4M guanidinium thiocyanate stock solution (J. Chirgwin et al., Biochemistry 18 (1979) 5295–5299), which had been preheated to 70° C., for one minute. The mixture was centrifuged at 10° C. for 10 minutes (Sorvall HB-4 rotor, 8,000 rpm). The supernatants were removed, 0.5 g of cesium chloride was added for each ml of supernatant and the mixture was heated at 60° C. for a few minutes. The resulting solution was then transferred to ultracentrifuge tubes which were one quarter full with a solution comprising 5.7M cesium chloride, 12.5 mM sodium salt of ethylenediaminetetraacetic acid (EDTA, pH 7.5) and 12.5 mM sodium citrate (pH 7.0). The tubes were centrifuged at 20° C. for 17 hours (Beckman SW-28 rotor, 21,000 rpm). The supernatants were removed by suction, and the sediment was suspended in TES buffer (50 mM tris.HCl, 10 mM EDTA, 0.2% (w/v) sodium salt of dodecylsulfate (SDS, pH 7.4)) with heating, and the suspension was extracted once with the same volume of a mixture of chloroform and n-butanol (4:1, v/v). After centrifugation, the aqueous phase was mixed with one tenth of the volume of 3M sodium acetate solution (pH 5.2), and precipitation was carried out with ethanol.

After standing at −20° C. for at least two hours, the mixture was centrifuged at 12,000 rpm and 0° C. for 20 minutes, and the sediment was washed with 80% strength ethanol. The dried precipitate was dissolved in 0.1 molar sodium acetate solution (pH 7.0) and re-precipitated with ethanol. The precipitate was, as described above, centrifuged, washed and dried. After redissolving in a buffer solution (0.1M sodium acetate, pH 5.2, 10 mM tris.HCl, pH 7.4, 1 mM EDTA and 0.2% (w/v) SDS), the solution was extracted twice with the same volume of phenol equilibrated with 1M tris.HCl, pH 8.0, and 0.2% (w/v) hydroxyquinoline, and was centrifuged. After extraction once with the same volume of chloroform, and centrifugation, the aqueous phase was mixed with the same volume of a solution of urea (8M) and lithium chloride (4M) and was stored at 0° C. overnight. After centrifugation at 0° C. for 20 minutes (SS 34 rotor, 10,000 rpm), the sediment was taken up in TES buffer, and the solution was mixed with one tenth the volume of 3M sodium acetate solution (pH 5.6), and precipitation with ethanol was carried out. The sediment was centrifuged, washed and dried as described above and finally taken up in buffer solution (50 mM tris.HCl, 1 mM EDTA, 0.1% w/v SDS, pH 7.5). The mixture was mixed with the same volume of 1M sodium chloride solution, and the poly(A)-RNA was isolated by chromatography twice on oligo-(dT)-cellulose. After addition of sodium acetate solution, the poly(A)-RNA was precipitated with ethanol and finally dissolved at a concentration of 1 μg/μl of buffer solution (1 mM tris.HCl, 0.1 mM EDTA, pH 7.0).

EXAMPLE 2

Synthesis, cloning and screening of the cDNA

10 μg of poly(A)-RNA in 10 μl of the abovementioned buffer were heated at 70° C. for 3 minutes, cooled rapidly in ice-water, and used for the synthesis of the cDNA. The synthesis of the first strand in a final volume of 100 μl was carried out by the method of M. Wickens et al., J. Biol. Chem. 253 (1978) 2483–2495, making use of $^{32}$P-labeled thymidine triphosphate, with the RNase inhibitor RNasin (100 U per mix; supplied by Biotec) additionally being used. In the synthesis of the second strand (likewise by the method of Wickens et al., loc. cit.), use was made of the Klenow fragment of DNA polymerase from *E. coli* (100 U/200 μl reaction), and the reaction was carried out at 15° C. for 4 hours and then at 20° C. for 2 hours. The reaction was stopped by extraction with a mixture of equal volumes of phenol and chloroform. The aqueous phase was centrifuged and then fractionated on a 5 ml column containing (®)SEPHADEX G-100, equilibrated in 20 mM sodium chloride. The fractions containing cDNA were collected and mixed with sodium acetate, and precipitation with ethanol was carried out overnight. To remove the hairpin structures, the dsDNA was treated with 90 U of nuclease S$_1$ (P-L Biochemicals) in a reaction volume of 250 μl at 37° C. for 30 minutes (Maniatis et al., Molecular Cloning, a Laboratory Manual; Cold Spring Harbor, 1982). The reaction was stopped by extraction with a mixture of equal volumes of phenol and chloroform and, after addition of sodium acetate, the DNA was precipitated with ethanol. The ends of the dsDNA were repaired in a known manner using Klenow polymerase (Maniatis et al., loc. cit.), the reaction was stopped by extraction with a mixture of equal volumes of phenol and chloroform and, after addition of sodium acetate, the DNA was precipitated with ethanol.

For the transformation of E. coli HB 101, standard methods were used for cleavage of the plasmid pUC13 (BRL, Catalogue and Reference Guide, 1983, page 89) with the restriction endonuclease Sma I and treatment with alkaline phosphatase. The ds-cDNA which was obtained was, without further pretreatment, dissolved in buffer (1 mM tris.HCl, pH 7.5, 0.1 mM EDTA) and ligated into the vector pUC13 which had been cleaved with Sma I and phosphorylated.

The transformation into E. coli HB 101 was carried out by described methods (Maniatis et al., loc. cit.). Ampicillin-resistant colonies were blotted onto nitrocellulose filters. Replica plates were treated with 150 µg/ml chloramphenicol, and the colonies were lyzed. The immobilization of the DNA on the nitrocellulose filters was carried out in a known manner (Maniatis et al., loc. cit).

For the in situ hybridization, 52 nitrocellulose filters, each with 300 to 400 colonies, were washed in prewashing solution (Maniatis et al., loc. cit., page 326) at 42° C. for 2 hours, and then batches of 26 filters were prehybridized at 42° C. for 6 hours in 150 ml of the following mixture:

0.9M NaCl
0.18M tris.HCl, pH 8.0
6 mM EDTA
5-fold concentrated Denhardt solution
0.2% (w/v) SDS
200 µg/ml sheared and denatured calf thymus DNA (Sigma)
200 µg/ml yeast RNA (Sigma)
0.5% (v/v) non-ionic surfactant (Nonidet P-40, Sigma)

The hybridization with $10^5$ cpm/ml of the probe with DNA sequence II was carried out with the same buffer (at 42° C. for 16 hours). The filters were then washed for 2×20 minutes at room temperature (0.9M sodium chloride, 0.09M sodium citrate, pH 7.0) and then washed in the same buffer for 2×20 minutes at 33° C. Thereafter the filters were dried and X-ray films were exposed to them at −70° C.

The probe with the DNA sequence II was synthesized by the phosphotriester method. For the hybridization, the oligonucleotide was labeled with $^{32}P$ at the 5'-end.

On screening, a recombinant plasmid (pL 10/2) which hybridized very strongly with the oligonucleotide of DNA sequence II and comprised about 1,500 bp of human DNA was isolated. The nucleotide sequence of the cDNA insert was determined by the method of Maxam and Gilbert (Methods in Enzymology 65 (1980) 499–560) as being nucleotides 518–2081 of DNA sequence I.

For 5'-prolongation of the clone pL 10/2, renewed cDNA synthesis with the poly(A)-RNA obtained in Example 1 was carried out:

The oligonucleotide of DNA sequence III

3' AGCTTCGCGTTGACTGTGGGGCCC    (III)

which corresponds to the nucleotide sequence 1051-1064 of the non-coding strand of DNA sequence I was synthesized by the phosphotriester method.

500 pmol of the oligonucleotide III, which had been reacted with polynucleotide kinase and $\gamma$-$^{32}P$-labeled ATP, and 10 µg of poly(A)-RNA from Example 1 were heated at 70° C. in 52 µl of buffer (1 mM tris.HCl, pH 7.5; 0.1 mM EDTA, 0.5M KCl) for 3 minutes and then cooled to 43° C. within 30 minutes. The cDNA was synthesized by the method of Gubler and Hoffman, Gene 25 (1983), 263–269, the oligonucleotide III acting as primer. The ends of the double-stranded cDNA were repaired using T4-DNA polymerase (P-L Biochemicals) by the method of Toole et al., Nature 312 (1984) 342–347.

After attachment of Hind III linkers of the formula IV

5' pGCAAGCTTGC 3'    (IV)

(BRL), which had been reacted with polynucleotide kinase and $\gamma$-$^{32}P$-labeled ATP, and after cleavage with Hind III, the cDNA was ligated into the vector pAT 153 (A. J. Twigg and D. Sherratt, Nature 283 (1980) 216–218) which had previously been treated with Hind III and alkaline phosphatase from calf intestines (Boehringer Mannheim). The transformation of E. coli HB 101, the amplification with chloramphenicol, and the lysis of the colonies were carried out as above.

The in situ colony hybridization was carried out as above the hybridization probe which was used being a 788 bp DNA fragment which was cut out of the plasmid pL 10/2 using the restriction enzyme Acc I and was labeled to a specific radioactivity of at least $10^8$ cpm/µg by nick translation (Maniatis et al., loc. cit.). The filters were washed as follows, for 15 minutes in each case:

in 6×SSC at room temperature
in 2×SSC at 42° C.
in 1×SSC at 50° C.
in 0.1×SSC at 50° C.
1×SSC=0.15M NaCl,
15 mM sodium citrate, pH 7.0.

2 strongly hybridizing clones were identified by screening. One of the clones (pH 14) contained an insert comprising about 1,060 bp of human DNA. The nucleotide sequence of this cDNA insert was determined by the method of Maxam and Gilbert, loc. cit.

By comparison of the cDNA sequences of the clones pH 14 and pL 10/2 it was found that pH 14 contains the 5'-terminal prolongation of pL 10/2 downstream of an overlap of about 480 bp (figure). pH 14 contains nucleotides 1–1062 of DNA sequence I.

EXAMPLE 3

Expression of the cDNA

The plasmid pH 14 is cut with Hind III and, partially, with BamHI, and the 841 bp Hind III-BamHI fragment is isolated after electrophoresis on a 1.4% agarose gel (low gel temperature agarose, BIO-RAD).

The plasmid pL 10/2 is cut with Hind III and BamHI, and the 4 kb Hind III-BamHI fragment is ligated with the 841 bp fragment from plasmid pH 14. This construct (plasmid phLS2) codes for a proteinase inhibitor which is prolonged by 9 amino acids at the N-terminal end. This expression plasmid permits, after transformation into E. coli and induction with isopropyl β-D-thiogalactopyranoside, the synthesis of the prolonged proteinase inhibitor, with control by the lac promotor-operator system.

Amino acid sequence I:
FIG. 1

1                                10
Gly Ser Lys Gly Pro Leu Asp Gln Leu Glu Lys Gly Gly

Amino acid sequence I:
FIG. 1

```
                    20
Glu Thr Ala Gln Ser Ala Asp Pro Gln Trp Glu Gln Leu
                            30
Asn Asn Lys Asn Leu Ser Met Pro Leu Leu Pro Ala Asp
40                                                 50
Phe His Lys Glu Asn Thr Val Thr Asn Asp Trp Ile Pro
                    60
Gly Glu Glu Glu Asp Asp Asp Tyr Leu Asp Leu Glu Lys
                        70
Ile Phe Ser Glu Asp Asp Asp Tyr Ile Asp Ile Val Asp
        80                                     90
Ser Leu Ser Val Ser Pro Thr Asp Ser Asp Val Ser Ala
                        100
Gly Asn Ile Leu Gln Leu Phe His Gly Lys Ser Arg Ile
                    110
Gln Arg Leu Asn Ile Leu Asn Ala Lys Phe Ala Phe Asn
            120                                130
Leu Tyr Arg Val Leu Lys Asp Gln Val Asn Thr Phe Asp
                        140
Asn Ile Phe Ile Ala Pro Val Gly Ile Ser Thr Ala Met
                        150
Gly Met Ile Ser Leu Gly Leu Lys Gly Glu Thr His Glu
                        160
Gln Val His Ser Ile Leu His Phe Lys Asp Phe Val Asn
170                                                180
Ala Ser Ser Lys Tyr Glu Ile Thr Thr Ile His Asn Leu
                        190
Phe Arg Lys Leu Thr His Arg Leu Phe Arg Arg Asn Phe
                        200
Gly Tyr Thr Leu Arg Ser Val Asn Asp Leu Tyr Ile Gln
        210                                    220
Lys Gln Phe Pro Ile Leu Leu Asp Phe Lys Thr Lys Val
                        230
Arg Glu Tyr Tyr Phe Ala Glu Ala Gln Ile Ala Asp Phe
                    240
Ser Asp Pro Ala Phe Ile Ser Lys Thr Asn Asn His Ile
            250                                260
Met Lys Leu Thr Lys Gly Leu Ile Lys Asp Ala Leu Glu
                        270
Asn Ile Asp Pro Ala Thr Gln Met Met Ile Leu Asn Cys
                        280
Ile Tyr Phe Lys Gly Ser Trp Val Asn Lys Phe Pro Val
                        290
Glu Met Thr His Asn His Asn Phe Arg Leu Asn Glu Arg
300                                                310
Glu Val Val Lys Val Ser Met Met Gln Thr Lys Gly Asn
                        320
Phe Leu Ala Ala Asn Asp Gln Glu Leu Asp Cys Asp Ile
                        330
Leu Gln Leu Glu Tyr Val Gly Gly Ile Ser Met Leu Ile
            340                                350
Val Val Pro His Lys Met Ser Gly Met Lys Thr Leu Glu
                    360
Ala Gln Leu Thr Pro Arg Val Val Glu Arg Trp Gln Lys
                    370
Ser Met Thr Asn Arg Thr Arg Glu Val Leu Leu Pro Lys
            380                                390
Phe Lys Leu Glu Lys Asn Tyr Asn Leu Val Glu Ser Leu
                        400
Lys Leu Met Gly Ile Arg Met Leu Phe Asp Lys Asn Gly
                    410
Asn Met Ala Gly Ile Ser Asp Gln Arg Ile Ala Ile Asp
                420
Leu Phe Lys His Gln Gly Thr Ile Thr Val Asn Glu Glu
430                                                440
Gly Thr Gln Ala Thr Thr Val Thr Thr Val Gly Phe Met
                        450
Pro Leu Ser Thr Gln Val Arg Phe Thr Val Asp Arg Pro
                    460
Phe Leu Phe Leu Ile Tyr Glu His Arg Thr Ser Cys Leu
        470                                    480
Leu Phe Met Gly Arg Val Ala Asn Pro Ser Arg Ser
```

DNA sequence I
FIG. 2

```
1
GT GGG AGC AAA GGC CCG CTG GAT CAG CTA
                    50
GAG AAA GGA GGG GAA ACT GCT CAG TCT GCA

GAT CCC CAG TGG GAG CAG TTA AAT AAC
            100
AAA AAC CTG AGC ATG CCT CTT CTC CCT GCC

GAC TTC CAC AAG GAA AAC ACC GTC ACC
        150
AAC GAC TGG ATT CCA GAG GGG GAG GAG

GAC GAC GAC TAT CTG GAC CTG GAG AAG
200
ATA TTC AGT GAA GAC GAC GAC TAC ATC

250
GAC ATC GTC GAC AGT CTG TCA GTT TCC

CCG ACA GAC TCT GAT GTG AGT GCT GGG

300
AAC ATC CTC CAG CTT TTT CAT GGC AAG

AGC CGG ATC CAG CGT CTT AAC ATC CTC

350
AAC GCC AAG TTC GCT TTC AAC CTC TAC

CGA GTG CTG AAA GAC CAG GTC AAC ACT
        400
TTC GAT AAC ATC TTC ATA GCA CCC GTT

GGC ATT TCT ACT GCG ATG GGT ATG ATT
        450
TCC TTA GGT CTG AAG GGA GAG ACC CAT

GAA CAA GTG CAC TCG ATT TTG CAT TTT
    500
AAA GAC TTT GTT AAT GCC AGC AGC AAG

TAT GAA ATC ACG ACC ATT CAT AAT CTC
550
TTC CGT AAG CTG ACT CAT CGC CTC TTC

600
AGG AGG AAT TTT GGG TAC ACA CTG CGG

TCA GTC AAT GAC CTT TAT ATC CAG AAG
                    650
CAG TTT CCA ATC CTG CTT GAC TTC AAA

ACT AAA GTA AGA GAG TAT TAC TTT GCT
```

-continued
DNA sequence I
FIG. 2

700
GAG GCC CAG ATA GCT GAC TTC TCA GAC

CCT GCC TTC ATA TCA AAA ACC AAC AAC

750
CAC ATC ATG AAG CTC ACC AAG GGC CTC

ATA AAA GAT GCT CTG GAG AAT ATA GAC

800
CCT GCT ACC CAG ATG ATG ATT CTC AAC

TGC ATC TAC TTC AAA GGA TCC TGG GTG

850
AAT AAA TTC CCA GTG GAA ATG ACA CAC

AAC CAC AAC TTC CGG CTG AAT GAG AGA

900
GAG GTA GTT AAG GTT TCC ATG ATG CAG

950
ACC AAG GGG AAC TTC CTG GCA GCA AAT

GAC CAG GAG CTG GAC TGC GAC ATC CTC

1000
CAG CTG GAA TAC GTG GGG GGC ATC AGC

ATG CTA ATT GTG GTC CCA CAC AAG ATG

1050
TCT GGG ATG AAG ACC CTC GAA GCG CAA

CTG ACA CCC CGG GTG GTG GAG AGA TGG

1100
CAA AAA AGC ATG ACA AAC AGA ACT CGA

GAA GTG CTT CTG CCG AAA TTC AAG CTG

1150
GAG AAG AAC TAC AAT CTA GTG GAG TCC

CTG AAG TTG ATG GGG ATC AGG ATG CTG

1200
TTT GAC AAA AAT GGC AAC ATG GCA GGC

1250
ATC TCA GAC CAA AGG ATC GCC ATC GAC

CTG TTC AAG CAC CAA GGC ACG ATC ACA

1300
GTG AAC GAG GAA GGC ACC CAA GCC ACC

-continued
DNA sequence I
FIG. 2

ACT GTG ACC ACG GTG GGG TTC ATG CCG

1350
CTG TCC ACC CAA GTC CGC TTC AGT GTC

GAC CGC CCC TTT CTT TTC CTC ATC TAC

1400
GAG CAC CGC ACC AGC TGC CTG CTC TTC

ATG GGA AGA GTG GCC AAC CCC AGC AGG

TCC TAG AGGTGGAGGTCTAGGTGTCTGAAGTGCC
TTGGGGGCACCCTCATTTTGTTTCCATTCCAACAA
CGAGAACAGAGATGTTCTGGCATCATTTACGTAG
TTTACGCTACCAATCTGAATTCGAGGCCCATATG
AGAGGAGCTTAGAAACGACCAAGAAGAGAGGCTT
GTTGGAATCAATTCTGCAATAGCCCATGCTG
TAAGCTCATAGAAGTCACTGTAACTGTAGTGTG
TCTGCTGTTACCTAGAGGGTCTCACCTCCCCACT
CTTCACAGCAAACCTGAGCAGCGCGTCCTAAGC
ACCTCCCGCTCCGGTGACCCCATCCTTGCACACC
TGACTCTGTCACTCAAGCCTTTCTCCACCAGGCC
CCTCATCTGAATACCAAGCACAGAAATGAGTGG
TGTGACTAATTCCTTACCTCTCCCAAGGAGGG
TACACAACTAGCACCATTCTTGATGTCCAGGG
AAGAAGCCACCTCAAGACATATGAGGGGTGCCC
TGGGCTAATGTTAGGGCTTAATTTTCTCAAAGCC
TGACCTTTCAAATCCATGATGAATGCCATCAG
TCCCTCCTGCTGTTGCCTCCCTGTGACCTGGAGG
ACAGTGTGTGCCATGTCTCCCATACTAGAGA
TAAATAAAT

I claim:

1. A cDNA coding for a protein that comprises amino acid sequence I represented by the formula:

```
1                                          10
Gly Ser Lys Gly Pro Leu Asp Gln Leu Glu Lys Gly Gly
                          20
Glu Thr Ala Gln Ser Ala Asp Pro Gln Trp Glu Gln Leu
                  30
Asn Asn Lys Asn Leu Ser Met Pro Leu Leu Pro Ala Asp
40                                         50
Phe His Lys Glu Asn Thr Val Thr Asn Asp Trp Ile Pro
                                  60
Glu Gly Glu Glu Asp Asp Asp Tyr Leu Asp Leu Glu Lys
                  70
Ile Phe Ser Glu Asp Asp Tyr Ile Asp Ile Val Asp
         80                               90
Ser Leu Ser Val Ser Pro Thr Asp Ser Asp Val Ser Ala
                                  100
Gly Asn Ile Leu Gln Leu Phe His Gly Lys Ser Arg Ile
                                  110
Gln Arg Leu Asn Ile Leu Asn Ala Lys Phe Ala Phe Asn
                                          120        130
Leu Tyr Arg Val Leu Lys Asp Gln Val Asn Thr Phe Asp
                                  140
Asn Ile Phe Ile Ala Pro Val Gly Ile Ser Thr Ala Met
                          150
Gly Met Ile Ser Leu Gly Leu Lys Gly Glu Thr His Glu
                  160
Gln Val His Ser Ile Leu His Phe Lys Asp Phe Val Asn
170                                         180
Ala Ser Ser Lys Tyr Glu Ile Thr Thr Ile His Asn Leu
                                  190
Phe Arg Lys Leu Thr His Arg Leu Phe Arg Arg Asn Phe
                          200
Gly Tyr Thr Leu Arg Ser Val Asn Asp Leu Tyr Ile Gln
         210                              220
Lys Gln Phe Pro Ile Leu Leu Asp Phe Lys Thr Lys Val
                                  230
Arg Glu Tyr Tyr Phe Ala Glu Ala Gln Ile Ala Asp Phe
```

-continued

| | | | | | | | | | |
|---|---|---|---|---|---|---|---|---|---|
240
Ser Asp Pro Ala Phe Ile Ser Lys Thr Asn Asn His Ile
250                                              260
Met Lys Leu Thr Lys Gly Leu Ile Lys Asp Ala Leu Glu
                                    270
Asn Ile Asp Pro Ala Thr Gln Met Met Ile Leu Asn Cys
                                                280
Ile Tyr Phe Lys Gly Ser Trp Val Asn Lys Phe Pro Val
                        290
Glu Met Thr His Asn His Asn Phe Arg Leu Asn Glu Arg
300                                              310
Glu Val Val Lys Val Ser Met Met Gln Thr Lys Gly Asn
                                    320
Phe Leu Ala Ala Asn Asp Gln Glu Leu Asp Cys Asp Ile
                330
Leu Gln Leu Glu Tyr Val Gly Gly Ile Ser Met Leu Ile
    340                                          350
Val Val Pro His Lys Met Ser Gly Met Lys Thr Leu Glu
                                360
Ala Gln Leu Thr Pro Arg Val Val Glu Arg Trp Gln Lys
                    370
Ser Met Thr Asn Arg Thr Arg Glu Val Leu Leu Pro Lys
            380                              390
Phe Lys Leu Glu Lys Asn Tyr Asn Leu Val Glu Ser Leu

400
Lys Leu Met Gly Ile Arg Met Leu Phe Asp Lys Asn Gly
                                410
Asn Met Ala Gly Ile Ser Asp Gln Arg Ile Ala Ile Asp
                        420
Leu Phe Lys His Gln Gly Thr Ile Thr Val Asn Glu Glu
430                                              440
Gly Thr Gln Ala Thr Thr Val Thr Thr Val Gly Phe Met
                                            450
Pro Leu Ser Thr Gln Val Arg Phe Thr Val Asp Arg Pro
                                    460
Phe Leu Phe Leu Ile Tyr Glu His Arg Thr Ser Cys Leu
470                                              480
Leu Phe Met Gly Arg Val Ala Asn Pro Ser Arg Ser.

2. A cDNA as claimed in claim 1, obtained by screening of a cDNA gene bank of human liver biopsy material using a probe of DNA sequence II

5' GGGTTGGCTACTCTGCCCATGAAGA 3'.

3. A cDNA as claimed in claim 1, comprising a DNA sequence I represented by the following formula:

```
                                                                        50
1
GT GGG AGC AAA GGC CCG CTG GAT CAG CTA GAG AAA GGA GGG GAA ACT GCT CAG TCT GCA GAT

100
CCC CAG TGG GAG CAG TTA AAT AAC AAA AAC CTG AGC ATG CCT CTT CTC CCT GCC GAC TTC CAC

150
AAG GAA AAC ACC GTC ACC AAC GAC TGG ATT CCA GAG GGG GAG GAG GAC GAC GAC TAT CTG GAC 200                                                           250
CTG GAG AAG ATA TTC AGT GAA GAC GAC GAC TAC ATC GAC ATC GTC GAC AGT CTG TCA GTT TCC

300
CCG ACA GAC TCT GAT GTG AGT GCT GGG AAC ATC CTC CAG CTT TTT CAT GGC AAG AGC CGG ATC

350
CAG CGT CTT AAC ATC CTC AAC GCC AAG TTC GCT TTC AAC CTC TAC CGA GTG CTG AAA GAC CAG

400
GTC AAC ACT TTC GAT AAC ATC TTC ATA GCA CCC GTT GGC ATT TCT ACT GCG ATG GGT ATG ATT 450                                                       500
TCC TTA GGT CTG AAG GGA GAG ACC CAT GAA CAA GTG CAC TCG ATT TTG CAT TTT AAA GAC TTT

550
GTT AAT GCC AGC AGC AAG TAT GAA ATC ACG ACC ATT CAT AAT CTC TTC CGT AAG CTG ACT CAT

600
CGC CTC TTC AGG AGG AAT TTT GGG TAC ACA CTG CGG TCA GTC AAT GAC CTT TAT ATC CAG AAG

650
CAG TTT CCA ATC CTG CTT GAC TTC AAA ACT AAA GTA AGA GAG TAT TAC TTT GCT GAG GCC CAG 700                                                       750
ATA GCT GAC TTC TCA GAC CCT GCC TTC ATA TCA AAA ACC AAC AAC CAC ATC ATG AAG CTC ACC

800
AAG GGC CTC ATA AAA GAT GCT CTG GAG AAT ATA GAC CCT GCT ACC CAG ATG ATG ATT CTC AAC

850
TGC ATC TAC TTC AAA GGA TCC TGG GTG AAT AAA TTC CCA GTG GAA ATG ACA CAC AAC CAC AAC
```

-continued

```
                              900
TTC CGG CTG AAT GAG AGA GAG GTA GTT AAG GTT TCC ATG ATG CAG ACC AAG GGG AAC TTC CTC
     950                                                                    1000
GCA GCA AAT GAC CAG GAG CTG GAC TGC GAC ATC CTC CAG CTG GAA TAC GTG GGG GGC ATC AGC
                                                 1050
ATG CTA ATT GTG GTC CCA CAC AAG ATG TCT GGG ATG AAG ACC CTC GAA GCG CAA CTG ACA CCC
                      1100
CGG GTG GTG GAG AGA TGG CAA AAA AGC ATG ACA AAC AGA ACT CGA GAA GTG CTT CTG CCG AAA
            1150
TTC AAG CTG GAG AAG AAC TAC AAT CTA GTG GAG TCC CTG AAG TTG ATC GGG ATC AGG ATC CTG
    1200                                                      1250
TTT GAC AAA AAT GGC AAC ATG GCA GGC ATC TCA GAC CAA AGG ATC GCC ATC GAC CTG TTC AAG
                                       1300
CAC CAA GGC ACG ATC ACA GTG AAC GAG GAA GGC ACC CAA GCC ACC ACT GTG ACC ACG GTG GGG
```

4. A cDNA as claimed in claim 3, comprising nucleotides 1 to about 1330 and from about 1340 to about 1442 of DNA sequence I, further comprising a DNA sequence that is selected from the group consisting of nucleotide sequences coding for Arg-Ser, Met-Ser, Val-Ser, Lys-Ala, Tyr-Ser and Leu-Met and that is located in the reading frame between about nucleotide 1330 and about 1340 of DNA sequence I.

5. A cDNA as claimed in claim 1, additionally coding for a signal peptide.

6. A cDNA as claimed in claim 2, additionally coding for a signal peptide.

7. A cDNA as claimed in claim 3, additionally coding for a signal peptide.

8. A cDNA as claimed in claim 4, additionally coding for a signal peptide.

9. A DNA sequence coding for a protein wherein said DNA sequence comprises at least one sequence selected from the group consisting of sequence encoding amino acids 1 to 443 and sequences encoding amino acids 446 to 480 of amino acid sequence I of claim 1.

10. A DNA sequence coding for a protein represented by the formula:

```
  1                              10                              20
Gly Ser Lys Gly Pro Leu Asp Gln Leu Glu Lys Gly Gly Glu Thr Ala Gln Ser Ala Asp Pro 30                              40
Gln Trp Glu Gln Leu Asn Asn Lys Asn Leu Ser Met Pro Leu Leu Pro Ala Asp Phe His Lys 50                              60
Glu Asn Thr Val Thr Asn Asp Trp Ile Pro Glu Gly Glu Glu Asp Asp Asp Tyr Leu Asp Leu 70                              80
Glu Lys Ile Phe Ser Glu Asp Asp Tyr Ile Asp Ile Val Asp Ser Leu Ser Val Ser Pro 90                              100
Thr Asp Ser Asp Val Ser Ala Gly Asn Ile Leu Gln Leu Phe His Gly Lys Ser Arg Ile Gln 110                             120
Arg Leu Asn Ile Leu Asn Ala Lys Phe Ala Phe Asn Leu Tyr Arg Val Leu Lys Asp Gln Val 130                             140
Asn Thr Phe Asp Asn Ile Phe Ile Ala Pro Val Gly Ile Ser Thr Ala Met Gly Met Ile Ser 150                             160
Leu Gly Leu Lys Gly Glu Thr His Glu Gln Val His Ser Ile Leu His Phe Lys Asp Phe Val 170                             180
Asn Ala Ser Ser Lys Tyr Glu Ile Thr Thr Ile His Asn Leu Phe Arg Lys Leu Thr His Arg 190                             200                           210
Leu Phe Arg Arg Asn Phe Gly Tyr Thr Leu Arg Ser Val Asn Asp Leu Tyr Ile Gln Lys Gln 220                             230
Phe Pro Ile Leu Leu Asp Phe Lys Thr Lys Val Arg Glu Tyr Tyr Phe Ala Glu Ala Gln Ile 240                             250
Ala Asp Phe Ser Asp Pro Ala Phe Ile Ser Lys Thr Asn Asn His Ile Met Lys Leu Thr Lys 260                             270
Gly Leu Ile Lys Asp Ala Leu Glu Asn Ile Asp Pro Ala Thr Gln Met Met Ile Leu Asn Cys
```

-continued

```
                     280                              290
Ile Tyr Phe Lys Gly Ser Trp Val Asn Lys Phe Pro Val Glu Met Thr His Asn His Asn Phe 300                              310
Arg Leu Asn Glu Arg Glu Val Val Lys Val Ser Met Met Gln Thr Lys Gly Asn Phe Leu Ala 320                              330
Ala Asn Asp Gln Glu Leu Asp Cys Asp Ile Leu Gln Leu Glu Tyr Val Gly Gly Ile Ser Met 340                              350
Leu Ile Val Val Pro His Lys Met Ser Gly Met Lys Thr Leu Glu Ala Gln Leu Thr Pro Arg 360                              370
Val Val Glu Arg Trp Gln Lys Ser Met Thr Asn Arg Thr Arg Glu Val Leu Leu Pro Lys Phe 380                              390
Lys Leu Glu Lys Asn Tyr Asn Leu Val Glu Ser Leu Lys Leu Met Gly Ile Arg Met Leu Phe 400                      410                              420
Asp Lys Asn Gly Asn Met Ala Gly Ile Ser Asp Gln Arg Ile Ala Ile Asp Leu Phe Lys His 430                              440
Gln Gly Thr Ile Thr Val Asn Glu Glu Gly Thr Gln Ala Thr Thr Val Thr Thr Val Gly Phe 450                              460
Met Pro Leu Ser Thr Gln Val Arg Phe Thr Val Asp Arg Pro Phe Leu Phe Leu Ile Tyr Glu 470                      480
His Arg Thr Ser Cys Leu Leu Phe Met Gly Arg Val Ala Asn Pro Ser Arg Ser:
```

11. A process for the production of a proteinase inhibitor which comprises:
(a) culturing an appropriate microbial host cell containing the DNA of claim 1 cloned into a vector capable of autonomous replication and expression of said DNA in said host under conditions sufficient to effect expression and production of said proteinase inhibitor; and
(b) recovering the proteinase inhibitor.

12. A process for the production of a proteinase inhibitor which comprises:
(a) culturing an appropriate microbial host cell containing the DNA of claim 2 cloned into a vector capable of autonomous replication and expression of said DNA in said host under conditions sufficient to effect expression and production of said proteinase inhibitor; and
(b) recovering the proteinase inhibitor.

13. A process for the production of a proteinase inhibitor which comprises: (a) culturing an appropriate microbial host cell containing the DNA of claim 3 cloned into a vector capable of automous replication and expression of said DNA in said host under conditions sufficient to effect expression and production of said proteinase inhibitor; and (b) recovering the proteinase inhibitor.

14. A process for the production of a proteinase inhibitor which comprises: (a) culturing an appropriate microbial host cell containing the DNA of claim 9 cloned into a vector capable of autonomous replication and expression of said DNA in said host under conditions sufficient to effect expression and production of said proteinase inhibitor; and (b) recovering the proteinase inhibitor.

15. A process for the production of a proteinase inhibitor which comprises: (a) culturing an appropriate microbial host cell containing the DNA of claim 5 cloned into a vector capable of autonomous replication and expression of said DNA in said host under conditions sufficient to effect expression and production of said proteinase inhibitor; and (b) recovering the proteinase inhibitor.

16. A process for the production of a proteinase inhibitor which comprises: (a) culturing an appropriate microbial host cell containing the DNA of claim 6 cloned into a vector capable of autonomous replication and expression of said DNA in said host under conditions sufficient to effect expression and production of said proteinase inhibitor; and (b) recovering the proteinase inhibitor.

17. A process for the (preparation of proteins or glycoptroeins comprising the steps of introducing DNA of claim 7 into an expression system and inducing the expression of said DNA in said expression system) production of a proteinase inhibitor which comprises: (a) culturing an appropriate microbial host cell containing the DNA of claim 8 cloned into a vector capable of autonomous replication and expression of said DNA in said host under conditions sufficient to effect expression and production of said proteinase inhibitor; and (b) recovering the proteinase inhibitor.

18. A process for the production of a proteinase inhibitor which comprises: (a) culturing an appropriate microbial host cell containing the DNA of claim 8 cloned into a vector capable of automous replicaion and expression of said DNA in said host under conditions sufficient to effect expression and production of said proteinase inhibitor; and (b) recovering the proteinase inhibitor.

* * * * *

UNITED STATES PATENT AND TRADEMARK OFFICE
CERTIFICATE OF CORRECTION

PATENT NO : 4,849,349

DATED : July 18, 1989

INVENTOR(S) : Hermann Ragg

It is certified that error appears in the above-identified patent and that said Letters Patent is hereby corrected as shown below:

Claim 3, between columns 13 7 14, 5th line from the top of page (the line with "1150", above it), the sexteenth triplet codon, change "ATC", to --ATG-- and at the same line, the twentieth triplet codon, chang e"ATC" to --ATG--.

Claim 3, between columns 13 7 14, 7th line from the top of the page, after "GGG" (last letters on 7th line form the top), the following should be entered.

```
                                         1350
TTC ATG CCG CTG TCC ACC CAA GTC CGC TTC ACT GTC GAC CGC CCC TTT CTT TTC CTC ATC TAC
                1400
GAG CAC CGC ACC AGC TGC CTG CTC TTC ATG GGA AGA GTG GCC AAC CCC AGC AGG TCC TAG

AGGTGGAGGTCTAGGTGTCTGAAGTGCCTTGGGGGCACCCTCATTTTGTTTCCATTCCAACAACGAGAACAGAGA

TGTTCTGGCATCATTTACGTAGTTTACGCTACCAATCTGAATTCGAGGCCCATATGAGAGGAGCTTAGAAACGACCAAG

AAGAGAGGCTTGTTGGAATCAATTCTGCACAATAGCCCATGCTGTAAGCTCATAGAAGTCACTGTAACTGTAGTGTGTC

TGCTGTTACCTAGAGGGTCTCACGTCCCCACTCTTCACAGCAAACCTGAGCAGCGCGTCCTAAGCACCTCCCGCTCCGG

TGACCCCATCCTTGCACACCTGACTCTGTCACTCAAGCCTTTCTCCACCAGGCCCCTCATCTGAATACCAAGCACAGAAA

TGAGTGGTGTGACTAATTCCTTACCTCTCCCAAGGAGGGTACACAACTAGCACCATTCTTGATGTCCAGGGAAGAAGCCA

CCTCAAGACATATGAGGGGTGCCCTGGGCTAATGTTAGGGCTTAATTTTCTCAAAGCCTGACCTTTCAAATCCATGATG

AATGCCATCAGTCCCTCCTGCTGTTGCCTCCCTGTGACCTGGAGGACAGTGTGTGCCATGTCTCCCATACTAGAGATAA

ATAAAT.
```

UNITED STATES PATENT AND TRADEMARK OFFICE
CERTIFICATE OF CORRECTION

PATENT NO  : 4,849,349

DATED      : July 18, 1989

INVENTOR(S) : Hermann Ragg

It is certified that error appears in the above-identified patent and that said Letters Patent is hereby corrected as shown below:

Column 1, line 11, change "an amino acids" to --an amino acid--.

Column 5, line 11, change "phosphorylated" to --dephosphorylated--.

Signed and Sealed this

Thirteenth Day of June, 1995

Attest:

BRUCE LEHMAN

Attesting Officer     Commissioner of Patents and Trademarks